(12) United States Patent
Castaldi et al.

(10) Patent No.: US 7,345,189 B2
(45) Date of Patent: Mar. 18, 2008

(54) PROCESS FOR THE PREPARATION OF ADAPALENE

(75) Inventors: Graziano Castaldi, Briona (IT); Pietro Allegrini, San Donato Milanese (IT); Gabriele Razzetti, Sesto S. Giovanni (IT); Mauro Ercoli, Milan (IT)

(73) Assignees: Dipharma S.p.A., Mereto di Tomba (IT); Lundbeck Pharmaceuticals, Italy, Padua (IT)

( * ) Notice: Subject to any disclaimer, the term of this patent is extended or adjusted under 35 U.S.C. 154(b) by 37 days.

(21) Appl. No.: 11/392,909

(22) Filed: Mar. 30, 2006

(65) Prior Publication Data

US 2006/0229465 A1   Oct. 12, 2006

(30) Foreign Application Priority Data

Apr. 1, 2005   (IT) ............... MI2005A0550

(51) Int. Cl.
 *C07C 69/76*   (2006.01)
(52) U.S. Cl. .................... 560/56; 560/100
(58) Field of Classification Search ............. 560/56, 560/100
See application file for complete search history.

(56) References Cited

U.S. PATENT DOCUMENTS 6,358,541 B1 *   3/2002   Goodman ............. 424/727

OTHER PUBLICATIONS

Dawson et al., Antagonist Analogue of 6-[3'-(1-Adamantyl)-4'-hydroxyphenyl]-2-naphthalenecarboxylic Acid (AHPN). Family of Apoptosis Inducers That Effectively Blocks AHPN- Induced Apoptosis but Not Cell-Cycle Arrest, J. Med. Chem, 2004, 47, 3518-3536.*

* cited by examiner

*Primary Examiner*—Yvonne Eyler
*Assistant Examiner*—Jennifer Y Cho
(74) *Attorney, Agent, or Firm*—Young & Thompson

(57) ABSTRACT

A process for the preparation of a compound of formula (I), or a salt thereof

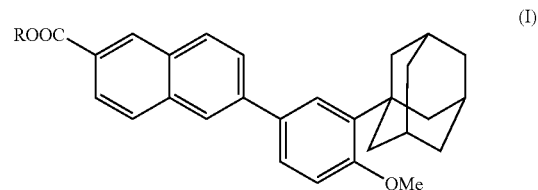

wherein R is H, $C_1$-$C_8$ alkyl, aryl or aryl-$C_1$-$C_8$ alkyl; comprising the reaction between a compound of formula (II)

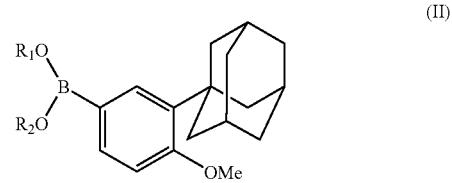

wherein $R_1$ and $R_2$ are independently hydrogen, $C_1$-$C_8$ alkyl, aryl, aryl-$C_1$-$C_8$ alkyl, or $R_1$ and $R_2$, taken together, form a —$(CH_2)_m$—V—$(CH_2)_n$— group, in which V is $NR_3$ or $C(R_3)_2$ wherein $R_3$ is hydrogen, $C_1$-$C_8$ alkyl, aryl or aryl-$C_1$-$C_8$ alkyl; and m and n, which can be the same or different, are 1 or 2; with a compound of formula (III)

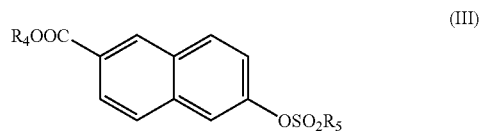

in which $R_4$ and $R_5$ are independently $C_1$-$C_8$ alkyl, aryl or aryl-$C_1$-$C_8$ alkyl; in the presence of a Ni (II) salt, an organic ligand and a basic agent, to obtain a compound of formula (I) wherein R is $C_1$-$C_8$ alkyl, aryl or aryl-$C_1$-$C_8$ alkyl and, if desired, its conversion to a compound of formula (I) wherein R is hydrogen or to a salt thereof.

13 Claims, No Drawings

PROCESS FOR THE PREPARATION OF ADAPALENE

FIELD OF THE INVENTION

The present invention relates to a process for the preparation of adapalene and intermediates useful in the synthesis thereof.

TECHNOLOGICAL BACKGROUND

Adapalene, namely 6-[3-(1-adamantyl)-4-methoxyphenyl]-2-naphthoic acid, having the following chemical formula:

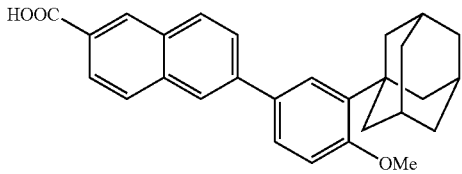

is disclosed in U.S. Pat. No. 4,717,720 and used in dermatology, in particular for the treatment of *acne vulgaris* and psoriasis.

According to U.S. Pat. No. 4,717,720 the synthesis is carried out by a coupling reaction between a magnesium, lithium or zinc derivative of a compound of formula (A) and a compound of formula (B), wherein X and Y are Cl, Br, F or I; R is hydrogen or alkyl; and Ad is 1-adamantyl

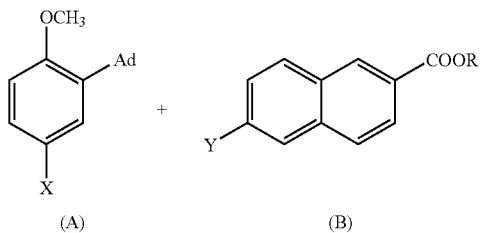

in an anhydrous solvent, in the presence of a metal transition or a complex thereof as a catalyst.

A number of alternative synthetic approaches have been suggested in order to reduce the preparation costs. Surprisingly, particularly advantageous proved the alternative synthesis of the invention, which makes use of easily-available, low-cost 6-hydroxy-2-naphthoic acid alkyl esters as intermediates, and provides good yields.

DISCLOSURE OF THE INVENTION

The object of the invention is a process for the preparation of a compound of formula (I), or a salt thereof

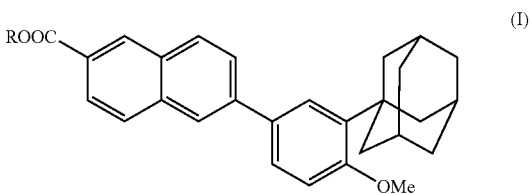

wherein R is H, $C_1$-$C_8$ alkyl, aryl or aryl-$C_1$-$C_8$ alkyl, comprising the reaction between a compound of formula (II)

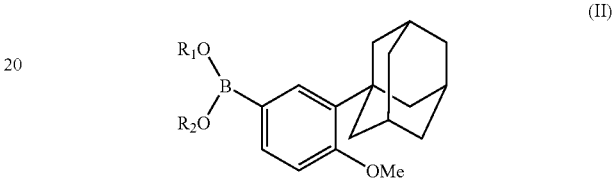

wherein $R_1$ and $R_2$ are independently hydrogen, $C_1$-$C_8$ alkyl, aryl, aryl-$C_1$-$C_8$ alkyl, or $R_1$ and $R_2$, taken together, form a —$(CH_2)_m$—V—$(CH_2)_n$— group, in which V is $NR_3$ or $C(R_3)_2$ wherein $R_3$ is hydrogen, $C_1$-$C_8$ alkyl, aryl or aryl-$C_1$-$C_8$ alkyl;

and m and n, which can be the same or different, are 1 or 2; with a compound of formula (III)

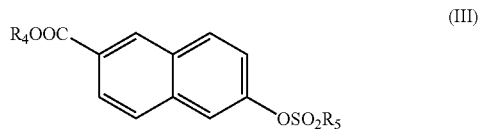

in which $R_4$ and $R_5$ are independently $C_1$-$C_8$ alkyl, aryl or aryl-$C_1$-$C_8$ alkyl;

in the presence of a Ni (II) salt, an organic ligand and a basic agent, to obtain a compound of formula (I) wherein R is $C_1$-$C_8$ alkyl, aryl or aryl-$C_1$-$C_8$ alkyl and, if desired, its conversion to a compound of formula (I) wherein R is hydrogen or to a salt thereof.

A salt of a compound of formula (I) is typically a pharmaceutically acceptable salt, for example an alkali metal salt, preferably the sodium salt.

A group or alkyl residue can be straight or branched. A $C_1$-$C_8$ alkyl group or residue is preferably $C_1$-$C_4$ alkyl, for example methyl, ethyl, propyl, isopropyl, butyl or tert-butyl, more preferably methyl or ethyl.

An aryl group is for example phenyl or naphthyl.

An aryl-$C_1$-$C_8$ alkyl group is preferably a benzyl or phenethyl group.

A Ni (II) salt is for example nickel (II) chloride, bromide, iodide, acetate, acetylacetonate, carbonate or hydroxide, preferably nickel chloride.

An organic ligand is typically a phosphine, such as tricyclohexylphosphine, triphenylphosphine, tris-(3-hydroxypropyl)phosphine, tributylphosphine, dppb (1,4-bis(diphenylphosphino)butane), dppp (1,4-bis(diphenylphosphino)propane), dppe (1,4-bis(diphenylphosphino)ethane) or dppf (diphenylphosphinoferrocene), preferably tricyclohexylphosphine or tris-(3-hydroxypropyl)phosphine.

A basic agent can be an organic base, such as a straight or branched tertiary amine, in particular diisopropyl-ethylamine or triethylamine, or an inorganic base, such as potassium or sodium carbonate, cesium carbonate, sodium acetate, sodium hydroxide, potassium or sodium phosphate, potassium hydrogen phosphate; preferably potassium or sodium carbonate and potassium or sodium phosphate, in particular potassium carbonate or phosphate.

The reaction can be carried out in the presence of an organic solvent, typically an aromatic hydrocarbon, such as toluene, xylene; an ether, such as tetrahydrofuran, methyltetrahydrofuran, dioxane; an ester, such as ethyl acetate or butyl acetate; or a mixture of two or more, typically 2 or 3, of said solvents or a mixture of one or more, typically 1, 2 or 3, thereof with water. The reaction is preferably carried out in a tetrahydrofuran/water mixture.

The stoichiometric ratio between the compounds of formula (II) and (III) can approximately range from 2 to 0.5 moles/mole; preferably from 2 to 1 moles/mole, more preferably from 1.3 to 1 moles/mole.

The stoichiometric ratio of compound (III) to basic agent approximately ranges from 1 to 5 moles/mole, preferably from 1.5 to 2.5 moles/mole.

The stoichiometric ratio of nickel salt to compound of formula (III) can approximately range from 0.5 to 0.01 moles/mole, preferably from 0.08 to 0.02 moles/mole.

The ratio of organic ligand to nickel salt can approx. range from 10 to 2 moles/mole, preferably from 6 to 3 moles/mole.

The reaction can be carried out at a temperature approx. ranging from 0° C. to the reflux temperature of the reaction mixture, preferably from 30° C. to the reflux temperature, more preferably at the reflux temperature of the mixture.

The conversion of a compound (I) in which R is $C_1$-$C_8$ alkyl, aryl or aryl-$C_1$-$C_8$ alkyl to another compound (I) in which R is hydrogen or a salt thereof can be carried out with known methods, for example as disclosed in U.S. Pat. No. 4,717,720.

A compound of formula (II), as defined above, in which $R_1$ and $R_2$ are hydrogen, can also exist in equilibrium with a polymeric dehydration form, typically trimeric (boroxine).

A compound of formula (II) can be obtained according to known methods. For example, a compound (II), wherein $R_1$ and $R_2$ are hydrogen or alkyl, can be obtained by reacting 3-(1-adamantyl)-4-methoxy-1-bromobenzene with n-BuLi and then with a tri-alkyl-borate; or by transforming 3-(1-adamantyl)-4-methoxy-1-bromobenzene into the corresponding Grignard reagent by reaction with magnesium and subsequent addition of tri-alkyl-borate; and, if desired, by hydrolizing the alkyl ester. The resulting acid can be then optionally converted to a corresponding ester (II) as defined above.

A compound (III) can be obtained according to known methods, starting from a 6-hydroxy-2-naphthoic acid ester, for example as taught by Green, T. "Protective Groups in Organic Synthesis", Ed. Wiley, III ed. page 197.

3-(1-Adamantyl)-4-methoxy-1-bromobenzene and 6-hydroxy-2-naphthoic acid are commercially available products.

A further object of the present invention is a highly pure crystalline compound of formula (I) or a salt thereof, as herein defined, as obtainable by the process of the invention. Highly pure compound is meant having a purity higher than 99.50%, especially higher than 99.95%.

The following examples illustrate the invention.

EXAMPLE 1

Synthesis of
6-[3-(1-adamantyl)-4-methoxyphenyl]-2-naphthoic
acid methyl ester [adapalene methyl ester]

A round-bottom flask is loaded with nickel (II) chloride (0.158 g; 1.2 mmol) and THF (20 ml), and tris(hydroxypropyl)phosphine (1.53 g; 7.3 mmol) is added to the mixture, which is refluxed for an hour, then cooled to a temperature of 50° C. and added in succession with methyl 6-tosylnaphthalene-2-carboxylate (8.7 g; 24.4 mmol), potassium phosphate (10.38 g; 48.8 mmol), 4-methoxy-3-adamantylphenylboronic acid (7-g; 24.4 mmol), water (0.88 g; 48.8 mmol) and THF (50 ml). The mixture is heated under reflux for 24 hours, then cooled to a temperature ranging from 50 to 55° C. and added with water, adjusting pH to a value below 7 with acetic acid. After cooling to a temperature of 15° C., the resulting product is filtered, thereby obtaining crystalline adapalene methyl ester (8.5 g; 20.08 mmol) in 82% yield.

$^1$H NMR: (300 MHz, DMSO), δ 8.6 (s, 1H), δ 8.3-7.8 (m, 6H), δ 7.7-7.5 (m, 2H), δ 7.1 (d, 1H), δ 3.9 (s, 3H), δ 3.85 (s, 3H), δ 2 (m, 9H), δ 1.7 (m, 6H).

EXAMPLE 2

Synthesis of
6-[3-(1-adamantyl)-4-methoxyphenyl]-2-naphthoic
acid sodium salt [adapalene sodium salt]

A round-bottom flask is loaded with adapalene methyl ester (7 g; 16.41 mmol), THF (42 ml), water (7 ml) and a 50% w/w sodium hydroxide aqueous solution (1.44 g; 18.05 mmol). The mixture is refluxed for 6 hours, then added with water (133 ml) and THF is distilled off to a residual content of approx. 5% w/w, heated to a temperature of about 80° C. until complete dissolution of the solid, then cooled to 15° C. The crystallized product is filtered and dried under vacuum in a static dryer at a temperature of 50° C., thereby obtaining adapalene sodium salt (6.7 g; 15.42 mmol) in 94% yield.

EXAMPLE 3

Synthesis of
6-[3-(1-adamantyl)-4-methoxyphenyl]-2-naphthoic
acid [adapalene]

A round-bottom flask is loaded with adapalene sodium salt (6.7 g; 15.42 mmol), THF (40 ml) and water (7 ml) and the mixture is refluxed until complete dissolution of the solid. The resulting solution is dropped into a 3% w/w acetic acid aqueous solution, keeping the temperature above 60-70° C., to precipitate adapalene acid (6.3 g; 15.27 mmol), which is filtered and dried under vacuum at a temperature of 50-60° C. The yield is 95%.

EXAMPLE 4

Synthesis of adapalene methyl ester

A round-bottom flask is loaded with nickel (II) chloride (0.158 g; 1.2 mmol) and THF (20 ml), and tris(hydroxypropyl)phosphine (1.53 g; 7.3 mmol) is added. The mixture is refluxed for an hour, then cooled to a temperature of 50° C. and added in succession with methyl 6-tosyl-naphthalene-2-carboxylate (8.7 g; 24.4 mmol), potassium phosphate (10.38 g; 48.8 mmol), 4-methoxy-3-adamantyl-phenylboronic acid (9.1 g; 31.8 mmol), water (10.53 g; 585.3 mmol) and THF (50 ml). The mixture is refluxed for 24 hours, then cooled to a temperature ranging from 50 to 55° C., added with water, and adjusted to pH lower than 7 with acetic acid. After cooling to 15° C., the resulting product is filtered, thereby obtaining adapalene methyl ester (9 g; 21.2 mmol) in 86% yield.

EXAMPLE 5

Synthesis of adapalene methyl ester

A round-bottom flask is loaded with nickel (II) chloride (0.158 g; 1.2 mmol) and THF (15 ml), and tris(hydroxypropyl)phosphine (1.53 g; 7.3 mmol) is added. The mixture is refluxed for an hour, then cooled to a temperature of 50° C. and added in succession with methyl 6-tosyl-naphthalene-2-carboxylate (8.7 g; 24.4 mmol), potassium carbonate (6.75 g; 48.8 mmol), 4-methoxy-3-adamantyl-phenylboronic acid (9.1 g; 31.8 mmol), water (8.11 g; 450.5 mmol) and THF (30 ml). The mixture is refluxed for 24 hours, then cooled to a temperature ranging from 50 to 55° C., added with water, and adjusted to pH lower than 7 with acetic acid. After cooling to 15° C., the resulting product is filtered, thereby obtaining adapalene methyl ester (9.37 g; 21.96 mmol) in 90% yield.

EXAMPLE 6

Synthesis of adapalene methyl ester

A round-bottom flask is loaded with methyl 6-tosyl-naphthalene-2-carboxylate (8.7 g; 24.4 mmol), THF (70 ml), potassium phosphate (10.38 g; 48.8 mmol), 4-methoxy-3-adamantyl-phenylboronic acid (7 g; 24.4 mmol), nickel chloride complexed with tri(cyclohexyl)phosphine (0.83 g; 1.2 mmol) and tri(cyclohexyl)phosphine (1.37 g; 4.88 mmol). The mixture is refluxed for 24 hours, then cooled to a temperature ranging from 50 to 55° C. and added with water, then cooled to 15° C. The resulting product is filtered, thereby obtaining adapalene methyl ester (8.1 g; 19.0 mmol) in 78% yield.

The invention claimed is:

1. A process for the preparation of a compound of formula (I), or a salt thereof

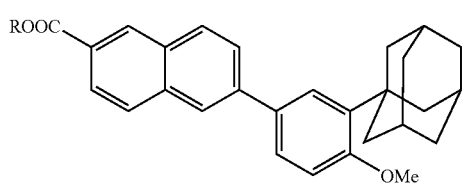

(I)

wherein R is H, $C_1$-$C_8$ alkyl, aryl or aryl-$C_1$-$C_8$ alkyl;

comprising the reaction between a compound of formula (II)

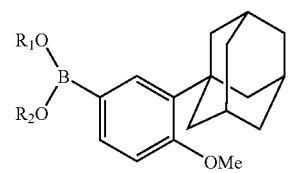

(II)

wherein $R_1$ and $R_2$ are independently hydrogen, $C_1$-$C_8$ alkyl, aryl, aryl-$C_1$-$C_8$ alkyl, or $R_1$ and $R_2$, taken together, form a —$(CH_2)_m$—V—$(CH_2)_n$— group, in which V is $NR_3$ or $C(R_3)_2$ wherein $R_3$ is hydrogen, $C_1$-$C_8$ alkyl, aryl or aryl-$C_1$-$C_8$ alkyl;

and m and n, which can be the same or different, are 1 or 2;

with a compound of formula (III)

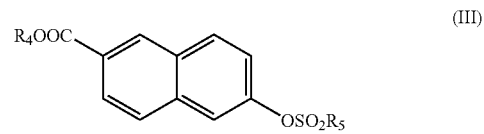

(III)

in which $R_4$ and $R_5$ are independently $C_1$-$C_8$ alkyl, aryl or aryl-$C_1$-$C_8$ alkyl;

in the presence of a Ni (II) salt, an organic ligand and a basic agent, to obtain a compound of formula (I) wherein R is $C_1$-$C_8$ alkyl, aryl or aryl-$C_1$-$C_8$ alkyl and, if desired, its conversion to a compound of formula (I) wherein R is hydrogen or to a salt thereof.

2. A process according to claim 1, wherein the Ni (II) salt is nickel (II) chloride, bromide, iodide, acetate, acetylacetonate, carbonate or hydroxide.

3. A process according to claim 1, wherein the organic ligand is a phosphine.

4. A process according to claim 3, wherein the phosphine is selected from tricyclohexylphosphine, triphenylphosphine, tris-(3-hydroxypropyl)phosphine, tributylphosphine, (1,4-bis(diphenylphosphino)butane), (1,4-bis (diphenylphosphino)propane), (1,4-bis (diphenylphosphino) ethane) and (diphenylphosphinoferrocene).

5. A process according to claim 4, wherein the phosphine is selected from tricyclohexylphosphine and tris-(3-hydroxypropyl)phosphine.

6. A process according to claim 1, wherein the basic agent is an organic or inorganic base.

7. A process according to claim 6, wherein the organic base is selected from a straight or branched tertiary amine and the inorganic base is selected from potassium or sodium carbonate, cesium carbonate, sodium acetate, sodium hydroxide, potassium or sodium phosphate and potassium hydrogen phosphate.

8. A process according to claim 7, wherein the inorganic base is selected from potassium or sodium carbonate and potassium or sodium phosphate.

9. A process according to claim 1, wherein the reaction is carried out in the presence of an organic solvent or a mixture of two or more organic solvents or a mixture of one or more organic solvents with water.

10. A process according to claim 1, wherein the stoichiometric ratio of a compound of formula (II) to a compound of formula (III) approximately ranges from 2 to 0.5 moles/mole.

11. A process according to claim 1, wherein the stoichiometric ratio of a compound of formula (III) to the basic agent approximately ranges from 1 to 5 moles/mole.

12. A process according to claim 1, wherein the stoichiometric ratio of a nickel salt to a compound of formula (III) approximately ranges from 0.5 to 0.01 moles/mole.

13. A process according to claim 1, wherein the ratio of the organic ligand to the nickel salt ranges from 10 to 2 moles/mole.

* * * * *